United States Patent
Pyo et al.

(10) Patent No.: US 7,751,052 B2
(45) Date of Patent: Jul. 6, 2010

(54) SURFACE PLASMON RESONANCE SENSOR CAPABLE OF PERFORMING ABSOLUTE CALIBRATION

(75) Inventors: Hyeon-Bong Pyo, Daejon (KR); Seon-Hee Park, Daejon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 302 days.

(21) Appl. No.: 11/949,744

(22) Filed: Dec. 3, 2007

(65) Prior Publication Data
US 2008/0130004 A1 Jun. 5, 2008

(30) Foreign Application Priority Data
Dec. 4, 2006 (KR) ............ 10-2006-0121204
Sep. 4, 2007 (KR) ............ 10-2007-0089412

(51) Int. Cl.
*G01N 21/55* (2006.01)
(52) U.S. Cl. .................................. 356/445
(58) Field of Classification Search ........... None
See application file for complete search history.

(56) References Cited

U.S. PATENT DOCUMENTS

| 5,641,640 | A | 6/1997 | Hanning |
| 7,067,322 | B2 | 6/2006 | Corn et al. |
| 2003/0067612 | A1 | 4/2003 | Ivarsson |
| 2003/0189707 | A1 | 10/2003 | Naya et al. |
| 2005/0030543 | A1 | 2/2005 | Ohtsuka et al. |
| 2005/0052655 | A1 | 3/2005 | Jones et al. |

FOREIGN PATENT DOCUMENTS

| JP | 11-304693 | 11/1999 |
| KR | 20030047567 | 6/2003 |
| KR | 20040102847 | 12/2004 |

OTHER PUBLICATIONS

Pyo, Hyeon-Bong et al., "Multiplexed polymer surface plasmon sensor with integrated optical coupler", Smart Medical and Biomedical Sensor Technology III, XP-002468741 SPIE vol. 6007, pp. 60070W1-10, 2005.
Hyeon-Bong Pyo et al., "Multichannel Surface Plasmon Resonance Imaging and Analysis of Micropatterned Self-Assembled Monolayers and Protein Affinity Interactions," Langmuir, vol. 21, pp. 166-171, 2005.

*Primary Examiner*—Gregory J Toatley, Jr.
*Assistant Examiner*—Amanda H Merlino
(74) *Attorney, Agent, or Firm*—Rabin & Berdo, P.C.

(57) ABSTRACT

There is provided a surface plasmon resonance imaging sensor capable of performing absolute calibration comprising: a transparent substrate; a first prism and a second prism formed at one surface of the substrate and symmetrically positioned with reference to the center axis of the substrate; an optical system for providing light to the first and second prisms; and a light receiving part for detecting the light reflected from the substrate, wherein a surface plasmon resonance (SPR) angle change of an object to be measured by the first prism is measured, and a refractive index change on each pixel of the object is obtained as a two-dimensional difference image by the second prism.

18 Claims, 5 Drawing Sheets

SURFACE PLASMON RESONANCE SENSOR CAPABLE OF PERFORMING ABSOLUTE CALIBRATION

CROSS-REFERENCES TO RELATED APPLICATIONS

The present invention claims priority of Korean Patent Application Nos. 10-2006-0121204 and 10-2007-0089412, filed on Dec. 4, 2006, and Sep. 4, 2007, respectively, which are incorporated herein by reference.

BACKGROUND OF THE INVENTION

1. Field of the Invention

The present invention relates to a surface plasmon resonance (SPR) sensor; and more particularly, to a surface plasmon resonance imaging sensor (SPRI sensor) capable of performing absolute calibration of refractive index (RI) change for each pixel on the image that represents either intensity or angle change of the reflected light, according to the variation of the surface plasmon resonance conditions, i.e., the changes in refractive index and/or optical thickness of material adjacent to the metal layer.

2. Description of Related Art

Surface plasmons are referred to as a quantized, collective oscillation of free electrons propagating along the surface of thin metal film. Surface plasmons can be excited by a TM-polarized light impinging on a metal film through a high refractive index material, e.g. a glass prism, above the critical angle. Critical angle is defined as the angle above which a total internal reflection (TIR) occurs. At a given energy (wavelength), surface plasmon wavevector is completely determined by optical properties of metal and dielectric material adjacent to the metal layer. If the wavevector of incident light matches well with that of surface plasmons, the energy of light is completely transferred to the surface plasmon mode. This is called surface plasmon resonance (SPR). An incident angle at which an SPR occurs (SPR angle) is very sensitive to the refractive index change of the material adjacent to the metal film. SPR sensor can perform quantitative as well as qualitative analysis, and measure the thickness and concentration of the material to be measured from the refractive index change of the material which is adjacent to the metal layer, using the above-mentioned characteristics.

An attempt to apply SPR sensor as a biosensor was proposed for the first time by C. Nylander and B. Liedberg in 1982 [C. Nylander and B. Liedberg, "Gas Detection by means of Surface Plasmon Resonance", Sensors and Actuators 3, pp. 79-88, 1982]. Then, SPR sensor has been widely used as one of the typical non-labeling biosensor systems, which can measure the interaction of bio-molecules without a marker such as a fluorescent material. After the first commercialization by Bicore AB of Sweden in 1990, SPR sensor has been widely used as a typical non-labeled biosensor system by researchers in the field of bio-, chemical-, and biochemical industries (U.S. Pat. Nos. 5,641,640 and 5,965,456).

FIG. 1a is a cross-sectional view of a conventional angle-interrogated SPR sensor.

Referring to FIG. 1a, the conventional angle interrogated SPR sensor includes a transparent substrate 11, a metal layer 12 which usually vacuum evaporated on the transparent substrate 11, a prism 13 located under the substrate 11 to be optically coupled to the metal layer 12, a light source 14 emits light to the prism 13, and an optical detector 15 for detecting light reflected from the substrate 11. At this time, a material 16 to be measured is disposed on the metal layer 12. More importantly, to be coupled with surface plasmons, the incident light 14 must be TM-polarized, so at least one polarizer must be positioned on the optical path between light source 14 and optical detector 15.

Conventional SPR sensor usually measures the reflectivity of incident light, which goes through the prism coupler 13 as a function of angle and is sensitive to the surface plasmon coupling conditions. However, because the shape of incident light is point-like, it reflects only one point or one pixel on the upper surface of the transparent substrate 11 which is adjacent to the metal layer 12. Therefore, it is unpractical and time-consuming to illuminate all the surface point-by-point, to estimate or to calculate the thickness and/or refractive changes of spatially distributed sample surface 16.

In order to solve this problem, a surface plasmon resonance imaging (SPRI) sensor or a surface plasmon microscopy (SPM) was proposed for the first time in 1987 and in 1988, where the relative intensity difference of reflected light was measured for each pixel or point on the whole surface, at a fixed angle and wavelength. [Yeatman, E. and Ash, E. A., Electron Lett, 1987, 23, pp. 1091-1092, and Rothenhausler, B. and Knoll, W., Nature, 1988, 332, pp. 615-617].

FIG. 1b is a cross-sectional view of a conventional SPRI sensor.

Referring to FIG. 1b, the conventional SPRI sensor includes a transparent substrate 11, a metal layer 12 deposited on the substrate 11, a prism 13 located under the substrate to be optically coupled to the metal layer 12, a light source 14 for emitting light to the prism 13, and an optical detector 15 for the detection of light reflected from the substrate 11. At this time, an object 16 to be measured is disposed on the metal layer 12. More importantly, to be coupled with surface plasmons, the incident light 14 must be TM-polarized, so at least one polarizer must be positioned on the optical path between light source 14 and optical detector 15.

Conventional SPRI sensor exploits a spatially expanded and collimated light as a light source 14 to illuminate upper surface of the transparent substrate 11. To obtain a difference image of reflected light, which gives a measure of thickness and/or refractive index change for each pixel on the metal layer 12 at the same time, a two-dimensional light receiving device, e.g., a charge-coupled device (CCD) can be used to measure the intensity of reflected light from the substrate 11. Therefore it is possible to measure the relative thickness and/or refractive index changes of the whole surface of sample 16 simultaneously, which covers the metal layer 12.

Conventional SPRI sensor exploits a method of imaging the difference of reflected light, which is the relative difference in reflectivity for each pixel on the surface 11. The relative difference in reflectivity is caused by relative thickness and/or refractive index changes of the sample 16 for each pixel or each point of the sample surface, adsorbed on metal layer 12. However, because the magnitude of the difference in reflectivity strongly depends on the dielectric properties of material, i.e., refractive indices of the prism 13 and of metal layer 12, and also on the thickness of metal layer 12 at a given wavelength, it is not possible to estimate or calibrate absolute thickness and/or refractive index change of sample layer 16.

SUMMARY OF THE INVENTION

In order to circumvent this problem, it is an object to provide a surface plasmon resonance sensor capable of absolute calibration of thickness and/or refractive index changes for each pixel on the sensor surface, which manifests itself as a two-dimensional difference reflectivity images by a surface plasmon resonance imaging (SPRI) sensor.

An embodiment of the present invention is directed to provide a surface plasmon resonance imaging sensor capable of absolute calibration, including: a transparent substrate; a first prism and a second prism formed at one surface of the substrate and symmetrically positioned with reference to the center axis of the substrate; an optical system for providing light to the prism; and a light receiving part for detecting the light reflected from the substrate, wherein the surface plasmon resonance (SPR) angle change of an object to be measured through the first prism is measured, and relative difference reflectivity at a fixed angle and wavelength, the thickness and/or refractive index change on each pixel of the object is obtained as a two-dimensional difference image through the second prism using an expanded and collimated light.

As described above, a SPRI sensor for representing a two-dimensional image of spatial change in the refractive index of an object and the angle-interrogated SPR sensor to calibrate absolute changes in thickness and/or refractive changes precisely, e.g., by fitting the cross-cut of the obtained angle-shifted image to the theoretical Fresnel calculations are integrated in a single SPR sensor to perform absolute calibration of the thickness and/or refractive index change on each pixel of the image, thereby an extended application fields are expected.

In addition, the present invention can provide a means for measuring absolute thickness and/or refractive index change of a multiple array of biosensor Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

BRIEF DESCRIPTION OF THE DRAWINGS

FIG. 4 is a view showing the correspondence between a two-dimensional SPR angle shift image measured by the hemi-cylindrical prism in FIG. 2a in accordance with an exemplary embodiment of the present invention and the SPR curve measured by a conventional angle-interrogated SPR sensor shown in FIG. 1a.

DESCRIPTION OF SPECIFIC EMBODIMENTS

Figure 1A:
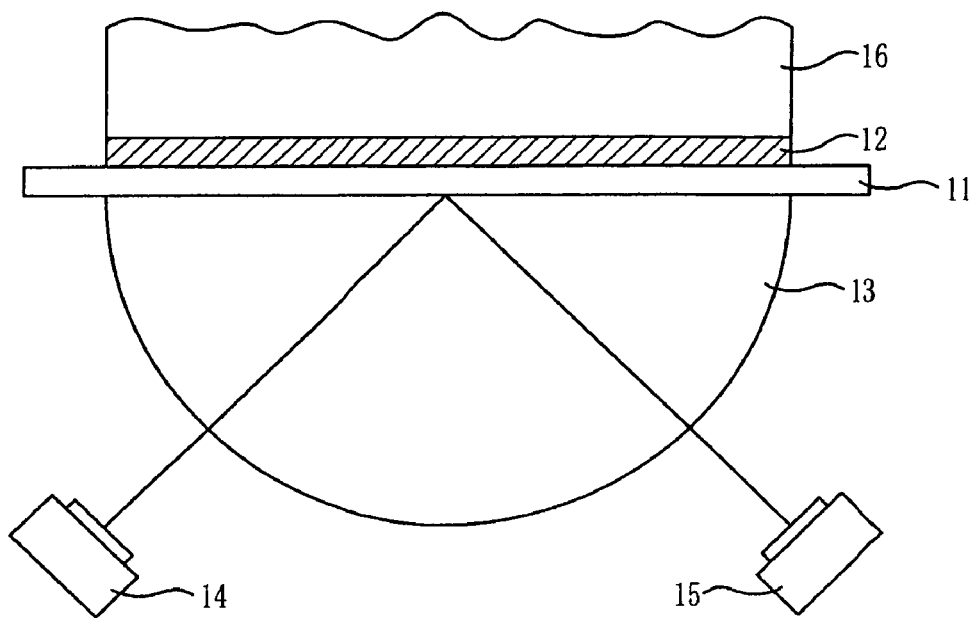
FIG. 1a is a cross-sectional view of a conventional angle-interrogated SPR sensor.

The advantages, features and aspects of the invention will become apparent from the following description of the embodiments with reference to the accompanying drawings, which is set forth hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity. In addition, when a layer is described to be formed on other layer or on a substrate, it means that the layer may be formed on the other layer or on the substrate or a third layer may be interposed between the layer and the other layer or the substrate. Like numbers refer to like elements throughout the specification.

The present invention discloses a means for solving problems of an SPRI sensor capable of obtaining spatial thickness and/or refractive index change of an object to be measured as a two-dimensional image, i.e., problems that cannot calibrate exactly the thickness and/or refractive index change on each pixel of the object. For this purpose, the present invention provides an SPR sensor for measuring a two-dimensional difference image in reflectivity of spatial variation of the refractive index of an object to be measured and an angle-interrogated SPR sensor for measuring the absolute thickness and/or refractive index change on each pixel of the object are integrated as a single chip.

Figure 2A:
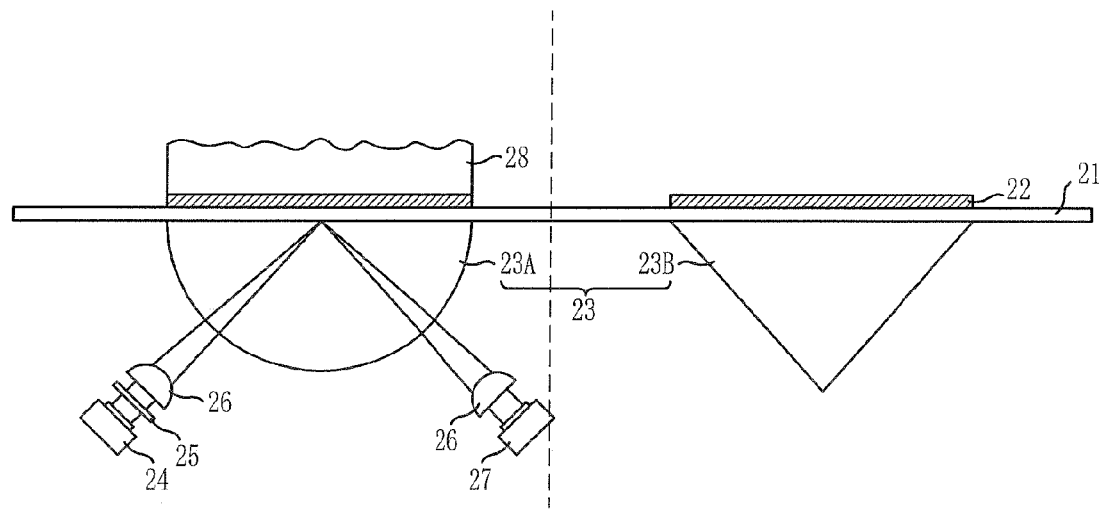
FIGS. 2a and 2b are cross-sectional views of an SPR sensor in accordance with an exemplary embodiment of the present invention.
Figure 2B:
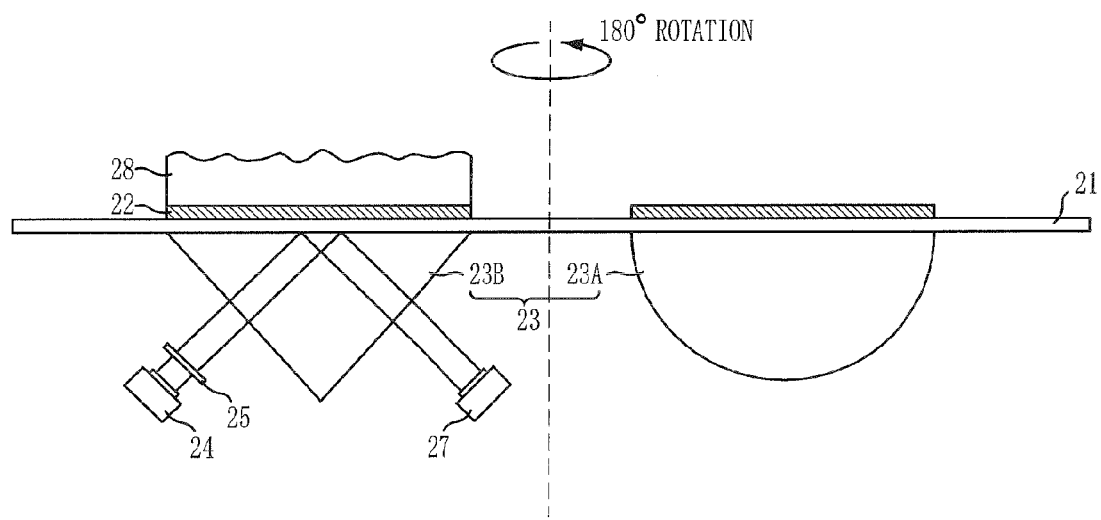

FIGS. 2a and 2b are cross-sectional views of an SPR sensor in accordance with an exemplary embodiment of the present invention; FIG. 2a illustrates an angle interrogated SPR sensor, and FIG. 2b illustrates an intensity-interrogated SPRI sensor.

As shown in FIGS. 2a and 2b, the SPR sensor in accordance with the present invention includes a transparent substrate 21, a first prism 23A and a second prism 23B formed at one surface of the substrate 21 and symmetrically positioned with reference to the center axis of the substrate 21, an optical system for providing light to the prism 23, and a light receiving part 27 for detecting the light reflected from the substrate 21. In addition, the SPR sensor further includes a metal layer 22, usually vacuum deposited on top of the substrate 21, on opposite side of the prism 23. As a plasmon-supporting material to be deposited on substrate 21 and formed a metal layer 22, any one from gold (Au), silver (Ag), copper (Cu), aluminum (Al) or from a semiconductor can be chosen. At this time, an object 28 to be measured is disposed on the metal layer 22.

The function of the prism 23 is to increase wavevector of incident light and to couple it to the surface plasmons, The first prism 23A may be a hemi-cylindrical prism, and the second prism 23B may be a triangular- or a trapezoidal prism.

The substrate 21 and the prism 23 have the same refractive index, and may be formed of a transparent material such as optical glass or optical plastic having the high refractive index of more than 1.5. At this time, as an optical glass it may be used BK7, SF10, SF11, LaSFN9 or the like, and as an optical plastic it may be used any one selected from the group consisting of polymethyl methacrylate (PMMA), polycarbonate (PC), and cyclic olefin copolymer (COC).

The SPR sensor in accordance with the present invention may further include an index matching oil or an elastomer interposed between the substrate 21 and the prism 23 to couple the substrate 21 to the prism 23 optically. At this time, when the substrate 21 and the prism 23 are optically coupled using an index matching oil or an elastomer, air bubbles may be developed between the substrate 21 and the prism 23, so the SPR image will be often smeared with them. Therefore, it is preferable to form the substrate 21 and the prism 23 in one body. For example, the substrate 21 and the prism 23 are injection molded using an optical plastic, to integrate the prism 23 to the substrate 21.

The optical system may include a light source 24, and a polarizer 25 which makes light emitted form the light source 24 in a transverse magnetic (TM) mode. At this time, the light source may use white right having a plurality of wavelengths or white light having a single wavelength, or may use any one selected from the group consisting of a laser, a light emitting diode, and a white light source having a spectral filter. Preferably, the light source 24 uses monochromatic light to fix the predefined SPR wavelength. Here, when the light source 24 is a point light source, the optical system may further include a beam expander with a plurality of the lenses for expanding and collimating the light in two-dimensional shape.

The polarizer 25 has functions to polarize the incident light in a TM mode and to couple it to a surface plasmon waves (SPWs), which are a surface confined TM mode waves. Therefore, in order to couple the surface plasmon wave with the incident light, the incident light should be polarized using the polarizer 25 before it reaches light receiving part 27.

In addition, the optical system may further include a means for the adjustment of incident angle range of light emitted from the light source 24, i.e., a focus adjustable lens 26.

The light receiving part 27 may be formed of any one selected from the group consisting of a photo-multiplier, a CCD camera, a photodiode array (PDA) and a photosensitive paper.

Further, in order to improve adhesion between the substrate 21 and the metal layer 22, the optical system may further include an adhesion layer formed between the substrate 21 and the metal layer 22. At this time, the adhesion layer may be formed of chromium (Cr) or titanium (Ti).

Figure 4:
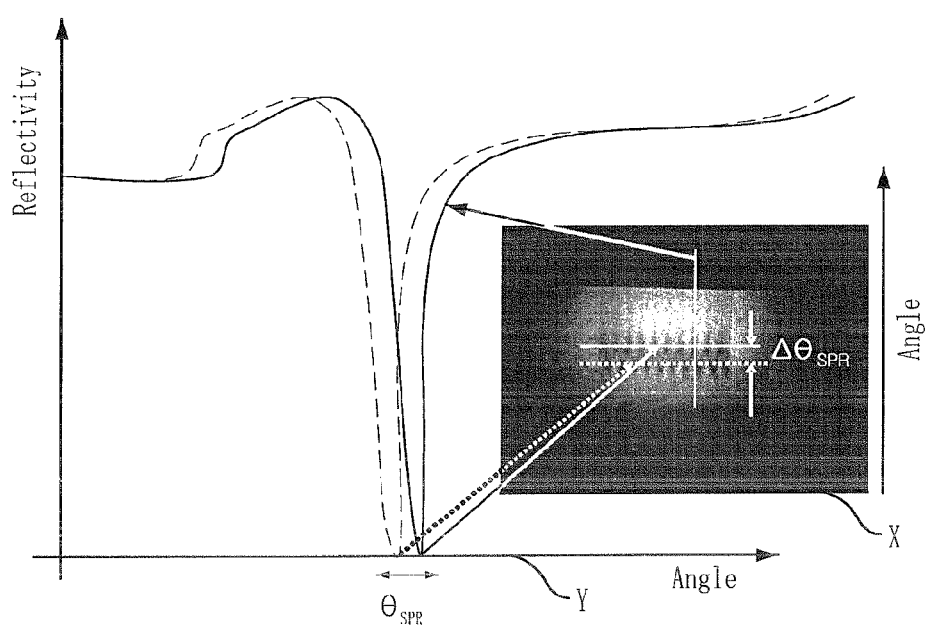

The SPR sensor in accordance with the present invention can measure the SPR angle change as a two-dimensional image as depicted in FIG. 4 through the first prism 23A, and obtain spatial variation in the refractive index of the object 28 through the second prism 23B as a two-dimensional image.

Hereinafter, operation principle of the SPR sensor in accordance with the present invention will be described. As described above, the SPR sensor in accordance with the present invention is a single SPR sensor in which an angle interrogated SPR sensor for measuring the precise thickness and/or refractive index change in each channel of different objects 28 which are formed on top of the metal layer 22, and an SPRI sensor for representing spatial variation in the refractive index of the object 28 as a two-dimensional image, are integrated.

First, referring to FIG. 2b, the SPRI sensor for measuring a two-dimensional image of the spatial variation in the refractive index of the object 28 can be achieved by impinging expanded, monochromatic, parallel, and collimated light on the second prism 23B. At this time, the optical system may include a light source 24, and a polarizer 25 for polarizing the light emitted from the light source 24, in a TM mode.

Specifically, in the SPR sensor system, the light emitted from the light source 24 can be expanded to illuminate the second prism 23B, and the system can make a difference reflectivity image which represents a spatial thickness and/or refractive index variation of the object 28 on each pixel using a multiplexed, light receiving device elements. At this time, the relative intensity of the difference reflectivity may depend on dielectric properties of the prism 23, of metal film 22, and on the thickness of metal film 22 together with wavelength and incident angle of the light source 24.

As described above, after obtaining the two-dimensional image of the variation in the refractive index of the object 28 by the second prism 23B, the substrate 21 is rotated with reference to a center axis of the substrate 21 in 180° such that the object 28 is located on top of the first prism 23A, thereby readily converting the SPRI sensor to the angle interrogated SPR sensor.

Next, referring to FIG. 2a, the angle interrogated SPR sensor for measuring the thickness and/or refractive index change of the object 28 has a means to adjust the focus of wedge-shaped monochromatic light that impinges on the first prism 23A, thereby the range of incident angle can be adjusted for proper conditions of the thickness and/or refractive index change measurement of the object 28. At this time, the optical system may include a light source 24, a polarizer 25 for polarizing the light emitted from the light source 24 in a TM mode, and a means for arbitrarily adjusting incident angle range of the light emitted from the light source 24, for example, a focus adjustable lens 26. In addition, since the angle interrogated SPR sensor in accordance with the present invention measures the variation in the refractive index of the object 28 using a wedge-shaped monochromatic light as a light source and possesses no moving parts in the system, a fast measurement of refractive index change of the object 28, adjacent to metal layer 22, is possible.

Specifically, the angle interrogated SPR sensor in accordance with the present invention adjusts an incident angle range of the light emitted from the light source 24 by using the focus adjustable lens 26 and measures SPR angle change due to variation of reflectivity. At this time, once SPR reflectivity curve is obtained as a function of incident angle and fitted to theoretical reflectivity values, calculated from Fresnel equation, it is possible to absolutely calibrate the variation in the refractive index.

Here, the reason why a resonant absorption of light, as a function of incident angle, takes place is due to the matching of surface plasmon wavevector and that of incident light, which goes through a prism 23A. Surface plasmon field decays exponentially away from metal 22-dielectric 28 interface, normal to both sides. Therefore, plasmon resonance conditions vary sensitively, depending on the refractive index change of the object 28 adjacent to metal layer 22.

Since the angle interrogated SPR sensor in accordance with the present invention measures variation in the SPR angle and reflectivity which depends on incident angle, it is needed to provide a means for arbitrarily adjusting the incident angle range. Therefore, in order to adjust the incident angle range of the light, the angle interrogated SPR sensor in accordance with the present invention uses a focus adjustable lens 26 to adjust the incident angle range.

Figure 3:
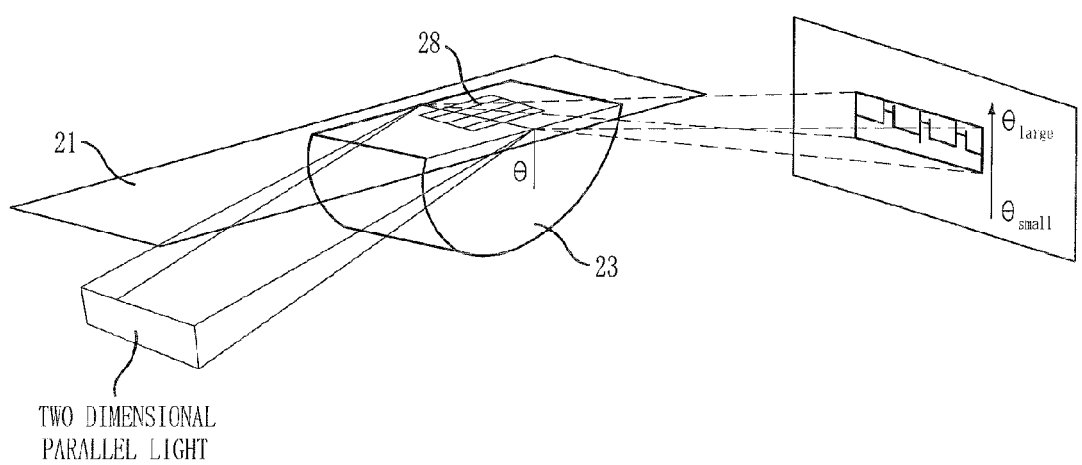
FIG. 3 is a perspective view schematically showing a measurement principle of an angle interrogated SPR sensor in accordance with an exemplary embodiment of the present invention.

FIG. 3 is a perspective view schematically showing a measurement principle of an angle interrogated SPR sensor in accordance with an exemplary embodiment of the present invention.

Referring to FIG. 3, in the case of the angle interrogated SPR sensor using two-dimensionally expanded monochromatic light as the incident light, it is possible to individually measure SPR angle change for each channel in real time, contrary to the case of conventional angle interrogated SPR sensor (see FIG. 1a). Therefore, a parallel, multiplexed detection is possible with higher throughput than that of conventional one.

FIG. 4 is a view showing the correspondence between a two-dimensional SPR angle shift image measured by the hemi-cylindrical prism in FIG. 2a in accordance with an exemplary embodiment of the present invention and the SPR curve measured by a conventional angle-interrogated SPR sensor shown in FIG. 1a.

Referring to FIG. 4, there is shown the correspondence between a two-dimensional SPR angle shift image representing spatial variation of the thickness and/or refractive index of the object measured by the SPRI sensor in accordance with the present invention and a graph representing the thickness and/or refractive index change depending on variation of the SPR angle measured by the conventional angle interrogated SPR sensor (see FIG. 1a). At this time, as shown in FIG. 4, it is possible to obtain a two-dimensional SPR angle shift image of the thickness and/or refractive index change of each channel of the object having a plurality of channels through the SPRI sensor in accordance with the present invention. In addition, a line profile of each channel corresponds to the graph of reflectivity vs. variation of the SPR angle.

Figure 1B:
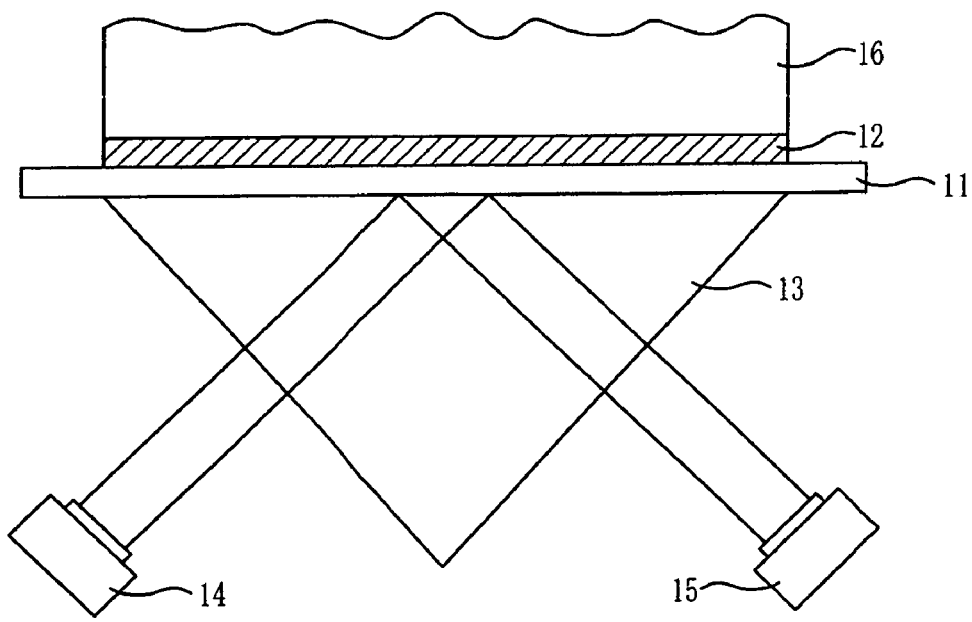
FIG. 1b is a cross-sectional view of a conventional intensity-interrogated SPRI sensor.
Figure 5:
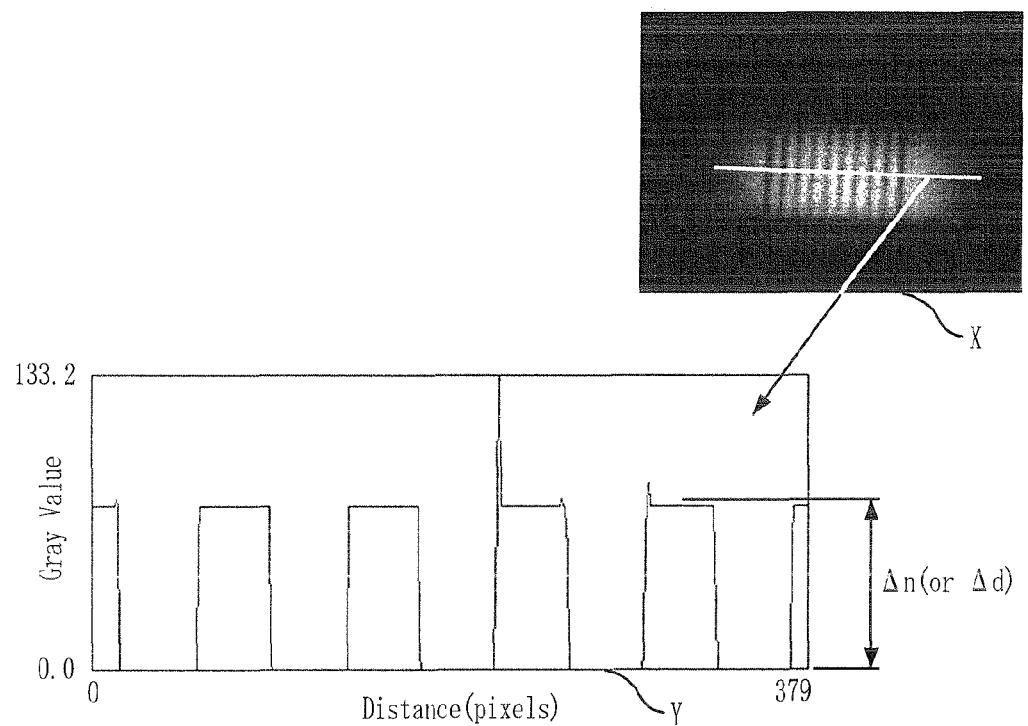
FIG. 5 is a view showing the correspondence between a two-dimensional difference intensity image at a fixed angle and wavelength measured by the triangular prism in FIG. 2b in accordance with an exemplary embodiment of the present invention and a line profile measured by a conventional intensity-interrogated SPRI sensor shown in FIG. 1b.

FIG. 5 is a view showing the correspondence between a two-dimensional difference intensity image at a fixed angle and wavelength measured by the triangular prism in FIG. 2b in accordance with an exemplary embodiment of the present invention and a line profile measured by a conventional intensity-interrogated SPRI sensor shown in FIG. 1b.

Referring to FIG. 5, it is shown that the correspondence between a two-dimensional difference intensity image measured by the SPRI sensor in accordance with the present invention and a graph representing a spatial profile of an object 28. Therefore, it is possible to confirm the correspondence between a two-dimensional difference intensity image measured by the SPRI sensor in accordance with the present invention and small variation in a refractive index of the object adjacent to metal layer obtained from a cross-section. In FIG. 5, Δn represents variation in a refractive index, and Δd represents variation in a thickness.

As can be seen from the foregoing, the SPRI sensor for representing a two-dimensional difference intensity image of spatial variation in a refractive index of the object and the angle interrogated SPR sensor for precisely measuring variation in a refractive index on each pixel of the object are integrated in a single SPR sensor to perform absolute calibration of the variation in the refractive index on each pixel of the image measured by the SPRI sensor, thereby more enlarging an application range of the SPRI sensor.

In addition, the present invention can provide a means for measuring absolute variation in a refractive index, such as a multiplexed biosensor or an imaging ellipsometer.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A surface plasmon resonance imaging sensor capable of absolute calibration comprising:
   a transparent substrate;
   a first prism and a second prism formed at one surface of the substrate and symmetrically positioned with reference to the center axis of the substrate;
   an optical system for providing light to the first and second prisms; and
   a light receiving part for detecting the light reflected from the substrate,
   wherein a surface plasmon resonance (SPR) angle change of an object to be measured by the first prism is measured, and a refractive index change on each pixel of the object is obtained as a two-dimensional difference image by the second prism and wherein absolute thickness and/or refractive index change on each pixel of the object is calibrated using the measurements taken by the first and second prism.

2. The surface plasmon resonance sensor of claim 1, wherein the first prism is a semi-cylindrical prism.

3. The surface plasmon resonance sensor of claim 1, wherein the second prism is a triangular prism or a trapezoidal prism.

4. The surface plasmon resonance sensor of claim 1, wherein the optical system adjusts a focus of wedge-shaped monochromatic light that impinges on the first prism.

5. The surface plasmon resonance sensor of claim 1, wherein the optical system measures a two-dimensional image of the spatial variation in the refractive index of the object by impinging a monochromatic, expanded and collimated light on the second prism.

6. The surface plasmon resonance sensor of claim 1, further comprising a metal layer, usually vacuum deposited on top of the substrate, on opposite side of the prism.

7. The surface plasmon resonance sensor of claim 6, wherein the metal layer is formed of any one from gold (Au), silver (Ag), and copper (Cu).

8. The surface plasmon resonance sensor of claim 1, wherein the surface and the first and second prisms are formed as one body.

9. The surface plasmon resonance sensor of claim 1, further comprising an index matching oil or an elastomer which is interposed between the substrate and the first and second prisms to couple the substrate to the prism optically.

10. The surface plasmon resonance sensor of claim 1, wherein the substrate and the first and second prisms are injection molded using an optical plastic to integrate the prism to the substrate.

11. The surface plasmon resonance sensor of claim 10, wherein an optical glass is BK7, SF10, SF11 or LasFN9.

12. The surface plasmon resonance sensor of claim 10, wherein the optical plastic is any one from polymethyl methacrylate (PMMA), polycarbonate (PC), polystyrene (PS), and cyclic olefin copolymer (coc).

13. The surface plasmon resonance sensor of claim 1, wherein the prism has the same refractive index as the substrate.

14. The surface plasmon resonance sensor of claim 1, wherein the optical system comprises:
   a light source; and
   a polarizer for polarizing the light emitted from the light source in a transverse magnetic (TM) mode.

15. The surface plasmon resonance sensor of claim 14, wherein the light source is any one from a laser, a light emitting diode and a white light source having a spectral filter.

16. The surface plasmon resonance sensor of claim 14, wherein the optical system further comprises a means for arbitrarily adjusting an incident angle of the light emitted from the light source.

17. The surface plasmon resonance sensor of claim 14, wherein the optical system further comprises a focus adjustable lens for adjusting an incident angle of the light emitted from the light source.

18. The surface plasmon resonance sensor of claim 1, wherein the light receiving part is any one from a photodiode, a photo-multiplier (PMT), a charge coupled device (CCD) camera, and a photosensitive paper.

* * * * *